(12) United States Patent
Effenhauser et al.

(10) Patent No.: US 7,760,346 B2
(45) Date of Patent: Jul. 20, 2010

(54) METHOD AND APPARATUS FOR ANALYZING A DRY-CHEMICAL TEST ELEMENT

(75) Inventors: Carlo Effenhauser, Weinheim (DE); Erich Haendler, Lampertheim (DE); Norbert Oranth, Hirschberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 133 days.

(21) Appl. No.: 12/206,803

(22) Filed: Sep. 9, 2008

(65) Prior Publication Data

US 2009/0086195 A1   Apr. 2, 2009

(30) Foreign Application Priority Data

Sep. 10, 2007   (EP)   ................... 07017650

(51) Int. Cl.
*G01J 1/00* (2006.01)
(52) U.S. Cl. .............. 356/213; 356/218; 356/433; 356/435
(58) Field of Classification Search ......... 356/213–218, 356/432–440
See application file for complete search history.

(56) References Cited

U.S. PATENT DOCUMENTS 4,125,372 A    11/1978   Kawai et al.
6,187,537 B1 *  2/2001   Zinn et al. ................ 435/6
6,707,554 B1    3/2004   Miltner et al.
2006/0077392 A1   4/2006   Hebert et al.

* cited by examiner

*Primary Examiner*—Hoa Q Pham
(74) *Attorney, Agent, or Firm*—Dinsmore & Shohl LLP

(57) ABSTRACT

The invention relates to a method and an apparatus for analyzing a dry-chemical test element, in particular an immunological test element, wherein, in the method, a dry-chemical test element is analyzed by optical scanning, whereby measurement light beams leaving assay regions of the test element, which are loaded with one or more immobilized optically active substances, with a respective measurement light intensity are detected by a detector device. The method comprises the following steps: during the optical scanning of a first assay region, from which the measurement light beams leave with a first measurement light intensity, a first quantity of light from measurement light beams which impinges on the detector device and a working range of the detector device are adapted to one another by selecting scanning parameters according to a first set of scanning parameters, and during the optical scanning of a second assay region, from which the measurement light beams leave with a second measurement light intensity which differs from the first measurement light intensity, a second quantity of light from measurement light beams which impinges on the detector device and the working range of the detector device are adapted to one another by selecting scanning parameters according to a second set of scanning parameters which differs from the first set of scanning parameters.

24 Claims, 3 Drawing Sheets

METHOD AND APPARATUS FOR ANALYZING A DRY-CHEMICAL TEST ELEMENT

FIELD OF THE INVENTION

The invention relates to a method and an apparatus for analyzing a dry-chemical test element, in particular an immunological test element.

BACKGROUND OF THE INVENTION

Such technologies are used to assay one or more analytes with which the dry-chemical test element is loaded. To this end, a plurality of assay regions are formed on the test element, for example in the form of strips or other areas such as circles or squares, in which the one or more analytes accumulate following the application of a quantity of a liquid sample to be assayed (cf., for example, U.S. Pat. No. 6,707,554 B1). Usually, the analytes are labelled directly and are thus prepared for a subsequent optical analysis of the dry-chemical test element. The preparation of the dry-chemical test element may optionally also include rinsing or washing with a buffer solution, a diluting solution or a washing solution. Finally, the dry-chemical test element can then be analyzed by optical scanning, in order to ascertain in particular the occurrence of one or more specific analytes in the assay regions of the test element.

During the optical scanning, measurement light beams which are produced in the scanned assay regions are detected by a detector device after leaving the assay regions. The measurement light beams can be produced by applying test light beams, which for their part are produced by a suitable monochromatic or polychromatic light source, to the assay regions which are loaded with optically active substances to be measured. In the assay regions, the light of the test light beams then interacts with the optically active substances, resulting in a corresponding change in the optical properties of the test light beams, which then leave the assay region as measurement light beams. When test light is applied, the transmission, the reflection or the fluorescence may be assayed as optical properties of the measurement light beams. Measurement light beams may also be based on a luminescence of the optically active substances in the assay regions.

A measurement light intensity, with which the measurement light beams leave a respective assay region, may be different for the analyzed assay regions. By way of example, a fluorescent light produced in the respective assay region by means of the test light beams may be emitted with a different intensity, which may for example be an indicator of the concentration of an analyte to be measured. The intensity of transmitted measurement light depends inter alia on the extent of the optical absorption in the observed assay region. In the case of assaying by means of fluorescence, the extent thereof depends inter alia also on the concentration of the 11 fluorescent molecules.

During the optical scanning of the dry-chemical test element, for example the test element and the detector device, by means of which the measurement light beams are detected, or the test element and the light source may be displaced relative to one another, in order thus to optically analyze assay region after assay region. According to the known procedure for optical scanning, certain scanning parameters are set before the start of the scanning process, with which a scan is then carried out. Usually a constant scanning speed and an exposure time for the detector device are set. If the measurement light beams are then emitted from the assay regions on the dry-chemical test element with a different intensity, the problem arises that in regions with a low measurement light intensity, which usually corresponds to a low concentration of the analyte to be measured, in some circumstances the scanning speed is too high to actually pick up a detected signal suitable for analysis. In other regions with a high analyte concentration, the light intensity of the measurement light beams leaving the assay region may in turn be so high that overloading of the detector device occurs at the preset scanning speed.

SUMMARY OF THE INVENTION

It is against the above background that the present invention provides certain unobvious advantages and advancements over the prior art. In particular, the inventors have recognized a need for improvements in methods and apparatus for analyzing a dry-chemical test element. Although the present invention is not limited to specific advantages or functionality, it is noted that the present invention provides an optimized analysis by optical scanning even when assay regions of the test element which are loaded with optically active substances to be measured have a different optical activity.

According to one aspect of the invention, there is provided a method for analyzing a dry-chemical test element, in particular an immunological test element, in which a dry-chemical test element is analyzed by optical scanning, whereby measurement light beams leaving, assay regions of the test element, which are loaded with one or more immobilized optically active substances, with a respective measurement light intensity are detected by means of a detector device, the method comprising the following steps: during the optical scanning of a first assay region, from which the measurement light beams leave with a first measurement light intensity, a first quantity of light from measurement light beams which impinges oh the detector device and a working range of the detector device are adapted to one another by selecting scanning parameters according to a first set of scanning parameters, and during the optical scanning of a second assay region, from which the measurement light beams leave with a second measurement light intensity which differs from the first measurement light intensity, a second quantity of light from measurement light beams which impinges on the detector device and the working range of the detector device are adapted to one another by selecting scanning parameters according to a second set of scanning parameters which differs from the first set of scanning parameters.

According to a further aspect of the invention, there is provided an apparatus for analyzing a dry-chemical test element, in particular an immunological test element, by optical scanning, the apparatus having the following features: a holder which is configured to hold a dry-chemical test element for analysis by optical scanning, a detector device which is configured to detect measurement light beams leaving assay regions, which are loaded with one or more immobilized optically active substances, with a respective measurement light intensity, and a control device which is configured to control the optical scanning of the dry-chemical test element as follows: during the optical scanning of a first assay region, from which the measurement light beams leave with a first measurement light intensity, a first quantity of light from measurement light beams which impinges on the detector device and a working range of the detector device are adapted to one another by selecting scanning parameters according to a first set of scanning parameters, and during the optical scanning of a second assay region, from which the measurement light beams leave with a second measurement light intensity which differs from the first measurement light intensity, a second quantity of light from measurement light beams which impinges on the detector device and the working range of the detector device are adapted to one another by selecting scanning parameters according to a second set of scanning parameters which differs from the first set of scanning parameters.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Figure 1:
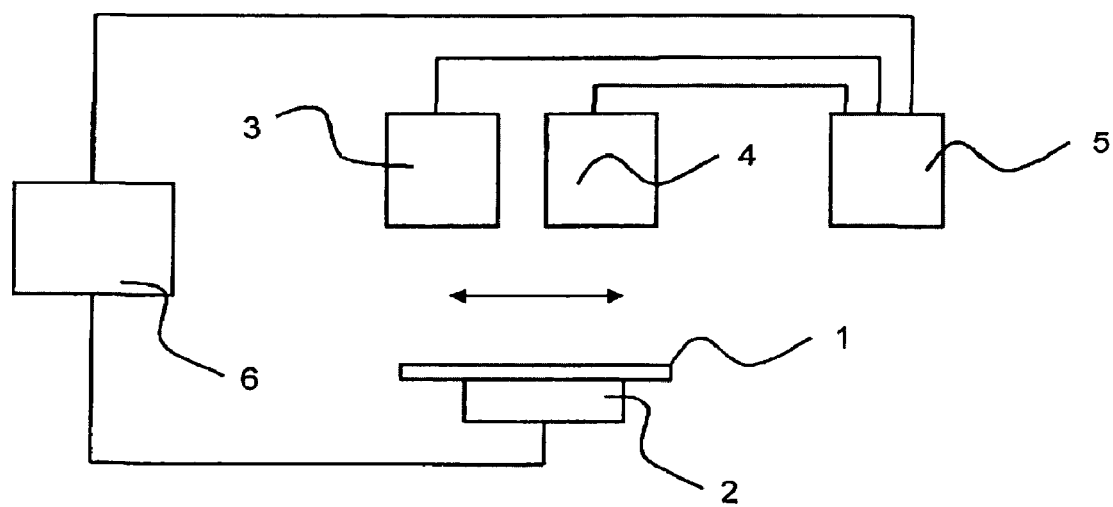
FIG. 1 shows a schematic diagram of an apparatus for analyzing a dry-chemical test element.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

By virtue of the invention, it is possible during a scanning process for analyzing the dry-chemical test element to individually adapt the optical scanning properties of the measurement system used, in particular of the optical components, to the optical activity of an assay region that is presently being analyzed. The quantity of light from measurement light beams which impinges on the detector device is controlled in such a way that the detector always operates in its predefined working range. Such a working range is usually predefined for detector devices, for example photodiodes, two-dimensional arrangements of photodiodes or photomultipliers, and can selectively be set by means of suitable electronic wiring of the detector. For the working range of the detector device, which is usually a range in which the electrical signal generated by the detector is linearly dependent on the impinging quantity of light, the detector device exhibits clear and reproducible behavior. If the quantity of light impinging on a detector surface lies outside the working range of the detector, which is also referred to as the dynamic range, usually no output signal can be observed due to too small a quantity of impinging light, or else the detector is overloaded, which leads to saturation effects or non-linearities. In this case, an electrical output signal, if it can even be distinguished from detector noise, is difficult or even impossible to evaluate in order to analyze the assay. It is also optionally possible for non-linear ranges to be assigned to the working range of the detector device if a reproducible response function of the detector device is known for this which allows an evaluation of the generated electrical output signals.

The measurement light beams may be detected in particular in the form of transmitted light beams, reflected light beams, scattered light beams or emitted light beams. The choice as to which and how many optical properties are analyzed can be made on a case-by-case basis taking account of the properties of the dry-chemical test element comprising the analytes to be assayed. Transmitted, reflected or scattered light beams are produced due to the fact that test light beams are applied to the assay region and said test light beams interact in the assay region with the immobilized optically active substances, as a result of which correspondingly changed measurement light beams are produced. However, emitted light beams may also be produced in this type of optical scanning, namely in the form of fluorescent or phosphorescent light. Furthermore, the optical scanning may comprise the detection of emitted light beams from the assay region or the assay regions, which for their part are the result of a bioluminescence, a chemoluminescence or an electro-chemoluminescence. In the case of bioluminescence or chemoluminescence, substances are added which trigger the emission of light beams in the form of luminescence by the optically active substances in the assay regions. By contrast, electrochemoluminescence is based on supplying electrical energy to the assay regions of the dry-chemical test element in order to generate luminescence of the optically active substances. In this embodiment of the method, suitable means are provided for supplying electrical energy to the assay regions, for example one or more electrodes.

The optically active substances are the result of a reaction of one or more reagents which are immobilized on the test element, wherein the reaction may be a binding reaction or a chemical reaction. As a result of the reaction, which takes place in the course of preparing the test element for the optical scanning process, the optically active substances are produced with properties which can be optically scanned. The binding reaction may be for example an immunological binding reaction or a hybridization reaction. Such reactions or chemical reactions may also occur multiple times. By means of one or more binding reactions, one or more reagents immobilized on the test element can be indirectly labelled. The presence of one or more reagents may also prevent the binding of labelled reagents.

For the changeover between the scanning parameters according to the first set of scanning parameters and the scanning parameters according to the second set of scanning parameters, one or more measures may be provided in order to accordingly set the quantity of light from measurement light beams which impinges on the detector device in both cases to the working range of the detector device. These measures also include for example the insertion or removal of optical filters into or from the path taken by the measurement light beams towards the detector device. The use of diaphragms may also be provided for example.

In principle, any measures can be used which make it possible to adapt the quantity of light impinging on the detector device to the working range of the detector device. It may even be provided in one embodiment to shift the working range by using an electronic wiring of the detector device, in order thus once again to achieve an adaptation between the impinging quantity of light and the working range. By way of example, in this connection, an amplification factor may be changed. The intervention with regard to the working range of the detector device may take place as an alternative or in addition to the measures for influencing the quantity of light impinging on the detector device. The adaptation of the working range of the detector device therefore forms part of the scanning parameters for the associated scanning process.

One typical further development of the invention provides that one or more variables selected from the following group of variables are set as scanning parameters: a scanning speed, an exposure time, a test light intensity of the test light beams, an amplification factor of the detector device and a supplying of the assay regions with electrical energy. The scanning speed relates to the speed at which the dry-chemical test element with the assay regions formed thereon on the one hand and the scanning device, which in particular comprises the detector device, on the other hand are moved relative to one another. As an alternative or in addition, when using test light beams, it is possible to set the speed at which the test light beams pass over the assay regions. By means of these measures, for each assay region, an associated scanning time is obtained during which measurement light beams are detected by the detector device for the respective assay region. If the measurement light intensity of the measurement light beams leaving the assay region is relatively low, which usually indicates a low analyte concentration, the scanning speed can accordingly be selected to be low so as thus to allow a sufficient quantity of light from measurement light beams to impinge on the detector device. Conversely, the scanning speed can be increased if a higher measurement light intensity is ascertained for a different assay region. The exposure time is the time during which measurement light beams are detected by the detector device for an associated assay region. This is firstly influenced of course by the scanning speed. In addition, it is possible to switch on or off optical components which expose or cover a detector surface of the detector device for a predefined time period or a plurality of predefined time periods. By way of example, in this connection, an adjustable diaphragm may be provided. However, the light intensity with which the test light beams are applied to the dry-chemical test element to be analyzed also usually influences the intensity of the measurement light beams. This scanning parameter can therefore also be adapted.

In one embodiment of the invention, it may be provided that at least one scanning parameter is kept constant for the first and the second set of scanning parameters. The fewer the number of scanning parameters that have to be changed when changing between the first and the second set of scanning parameters, usually the quicker the changeover can take place.

One embodiment of the invention provides that a change from the scanning parameters according to the first set of scanning parameters to the scanning parameters according to the second set of scanning parameters is carried out in the course of a continued scanning process for the dry-chemical test element.

Typically, one development of the invention provides that the change from the scanning parameters according to the first set of scanning parameters to the scanning parameters according to the second set of scanning parameters takes place as a function of measurement information which is derived from a pre-scanning process carried out beforehand. The pre-scanning process carried out beforehand provides information about the optical activity of the individual assay regions on the dry-chemical test element, be this information about absolute or relative measurement parameters. Depending on this information, the sets of scanning parameters for the assay regions can then be set in order to carry out the change(s) accordingly during the optical scanning. The pre-scanning process may be carried out for example as a quick scan. In addition or as an alternative, it may be provided to carry out the pre-scanning process at a lower resolution than is then set for the following main scan. For the pre-scanning process, it is not necessary to use the dry-chemical test element that is, then actually to be analyzed; a model test element or standard test element with a comparable configuration of the assay regions may also be used.

In one embodiment of the invention, it may be provided that the change from the scanning parameters according to the first set of scanning parameters to the scanning parameters according to the second set of scanning parameters takes place as a function of current measurement information which is derived from current measured values during the optical scanning of the dry-chemical test element. A changeover between sets of scanning parameters can then be triggered presently and at short notice during the scanning process, even if a certain scanning behavior has already been set beforehand.

One further development of the invention may provide that a changeover between the scanning parameters according to the first set of scanning parameters and the scanning parameters according to the second set of scanning parameters takes place multiple times during the optical scanning of the dry-chemical test element. The multiple changeovers between sets of scanning parameters may take place automatically according to preset control parameters. However, as an alternative or in addition to this, a multiple changeover may also be triggered by current measurement information which is obtained during the scanning process.

One further development of the invention provides that the first assay region, after the optical scanning with the scanning parameters according to the first set of scanning parameters, is optically scanned again with the scanning parameters according to the second set of scanning parameters. The second optical scanning of the first assay region may be carried out immediately before the optical scanning of a subsequent assay region. However, a second optical scanning of the first assay region after the completion of one scan of the dry-chemical test element may also be provided. In this case, usually a return to the first assay region is then necessary. The second optical scanning of the first assay region may be carried out for example when it is ascertained that no signal or only a signal that is insufficient for analysis has been obtained on the detector device with the first set of scanning parameters. The first assay region is then analyzed again with a changed set of scanning parameters.

In accordance with yet another embodiment of the invention, it may be provided that test light application regions, which are respectively assigned to the assay regions, are formed in such a way as not to overlap during the optical scanning of the assay regions. The test light application regions are obtained as the regions on the dry-chemical test element which are passed over by test light beams during the scanning process in conjunction with the associated assay region. In this connection, it may be provided in one embodiment that the test light application regions are formed directly adjacent to one another, so that no regions free of exposure to test light are created between them.

Another embodiment of the invention provides that the first quantity of light is selected to lie in a first sub-range of the working range and the second quantity of light is selected to lie in a second sub-range of the working range which differs from the first sub-range. Typically, the first sub-range and the second sub-range are a lower and an upper sub-range of the working range. In this way, the working range or dynamic range of the detector device is exploited to the greatest possible extent.

Typically, one development of the invention provides that a plurality of identical assay regions are optically scanned in one scanning position and are detected in a two-dimensionally resolved manner. In connection with this embodiment use is made of a detector device which allows a two-dimensional resolution of the measurement light beams impinging on the detector surface. By means of this embodiment of the method, it is possible for example to measure a plurality of assay regions also transversely to the scanning direction.

In the various embodiments of the method, the image information obtained during the optical scanning may be processed according to a so-called stitching process. In this process, individual images are combined to form an overall image, with any image information which occurs multiple times, such as overlaps, advantageously being eliminated. The stitching may be carried out with the aid of suitable software tools, which are available as such in different variants.

With regard to the embodiments of the apparatus for analyzing a dry-chemical test element, the explanations given in connection with associated method variants apply accordingly.

In order that the invention may be more readily understood, reference is made to the following examples, which are intended to illustrate the invention, but not limit the scope thereof.

FIG. 1 shows a schematic diagram of an apparatus for analyzing a dry-chemical test element 1 by optical scanning. The optical analysis of the test element 1 on a support 2, which is in particular a holder for the test element 1, serves for the analytical detection of one or more optically active substances, in particular for medical diagnosis purposes, which are found in assay regions of the test element 1. The optically active substances are the result of a reaction of one or more reagents which are immobilized on the test element 1, wherein the reaction may be a binding reaction or a chemical reaction. As a result of the reaction, which takes place in the course of preparing the test element for the optical scanning process, the optically active substances are produced with properties which can be optically scanned. The binding reaction may be for example an immunological binding reaction or a hybridization reaction. Such reactions or chemical reactions may also occur multiple times. By means of one or more binding reactions, one or more reagents immobilized on the test element 1 can be indirectly labelled. The presence of one or more reagents may also prevent the binding of labelled reagents.

In the illustrated embodiment, test light beams are applied to the dry-chemical test element 1 from a test light source 3 for the optical scanning process. By means of a detector device 4, measurement light beams leaving the dry-chemical test element 1 are then detected. During the optical analysis, a relative movement takes place between the dry-chemical test element 1 and one or more of the optical components, in particular the test light source 3 or the detector device 4. A control device 5 is coupled to the detector device 4 and the test light source 3, which control device serves during the optical scanning to set in each case a suitable set of scanning parameters for the different assay regions on the dry-chemical test element 1. For this purpose, the control device 5 is also coupled to a displacement unit 6 which brings about the relative movement during the scanning process.

By means of the control device 5, the scanning parameters are set depending on the assay region on the dry-chemical test element 1 in such a way that the quantity of light impinging on the detector device 4 and a working range of the detector device 4 are adapted to one another. The scanning parameters that can be set include in particular the scanning speed, the exposure time for the detector device 4, the intensity of the test light beams and the setting of an amplification factor of the detector device.

Figure 2:
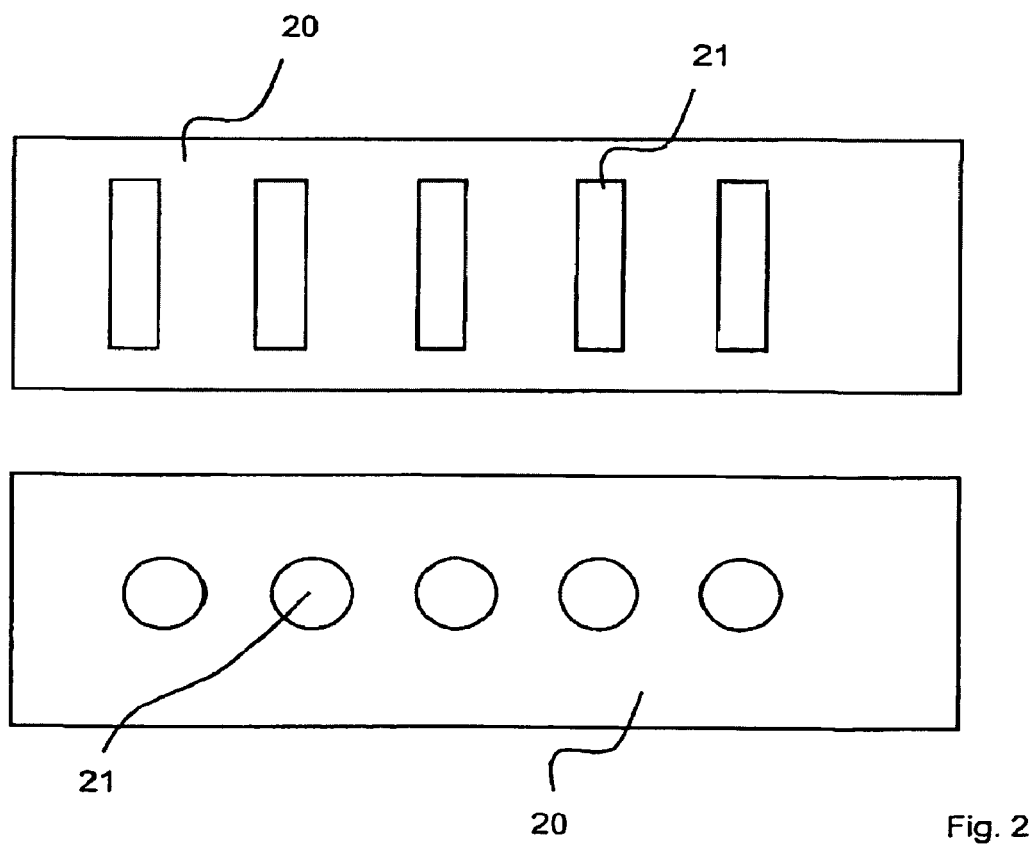
FIG. 2 shows examples of dry-chemical test elements.

FIG. 2 shows a schematic diagram of dry-chemical test elements, in which a plurality of assay regions 21 are formed on a substrate 20 which is designed for example as a membrane. The optically active substance(s) to be assayed are "trapped", i.e., immobilized, in the plurality of assay regions 21. A binding of the optically active substances in the assay regions 21 takes place in particular by means of antibodies which then interact with optically active labelling or marking molecules. The intensity with which measurement light beams leave the plurality of assay regions 21 during the optical scanning is then an indicator as to the extent to which one or more optically active substances is present in one of the plurality of assay regions 21.

Figure 3:
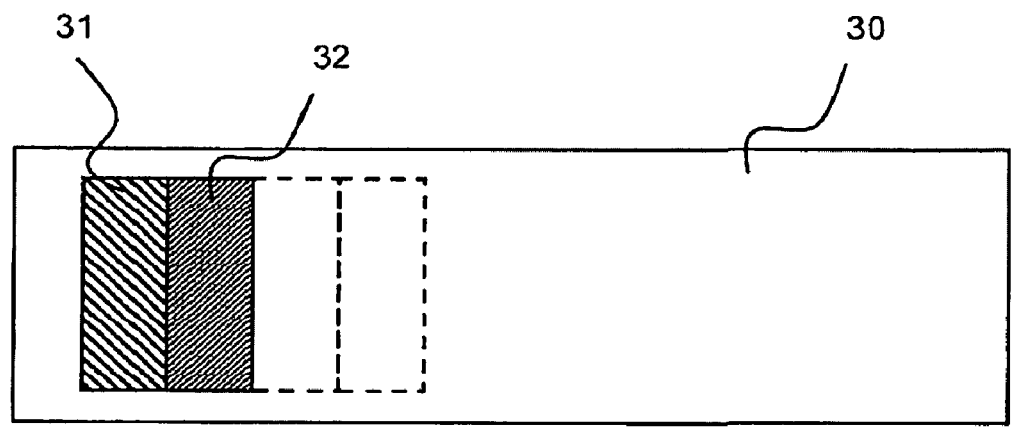
FIG. 3 shows a schematic diagram to explain a scanning process.

FIG. 3 shows a schematic diagram to explain a scanning process. Two test light application regions 31, 32 are shown schematically on the dry-chemical test element 30. These are the regions on the dry-chemical test element 30 which are passed over by the test light beams during the scanning of a respectively associated assay region. It can be seen that the test light application regions 31, 32 are formed adjacent to one another and so that they do not overlap. According to one embodiment, the optical scanning of the two test light application regions 30, 31 takes place with different sets of scanning parameters, for example a different scanning speed.

Figure 4:
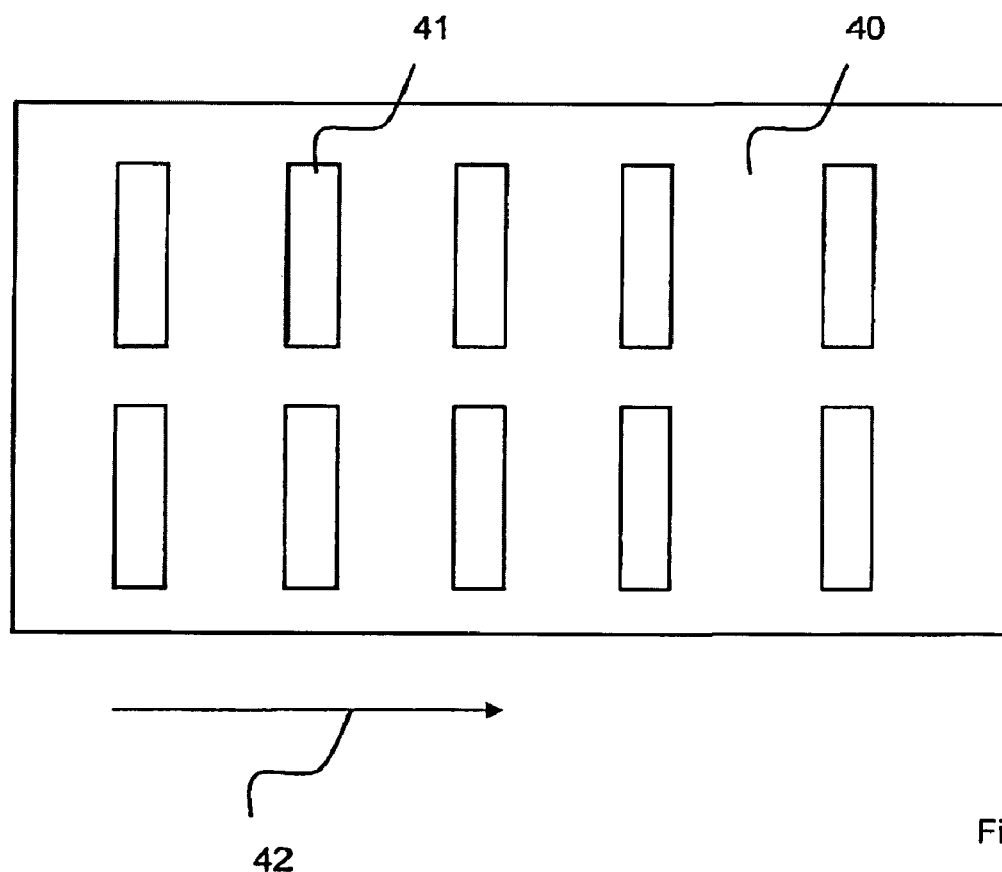
FIG. 4 shows a schematic diagram of a dry-chemical test element with a plurality of assay regions arranged transversely to the scanning apparatus.

FIG. 4 shows a schematic diagram of a dry-chemical test element 40, in which assay regions 41 extend not only along a scanning direction 42 but also transversely thereto. Given a suitable detector device, for example a two-dimensional diode arrangement, a spatial resolution may also take place transversely to the scanning direction 42 during the optical scanning of the dry-chemical test element 40. Assay regions 41 which are arranged one above the other belong to a "same signal class", which means that they emit measurement light beams with the same or similar intensity and can thus be analyzed with the same set of scanning parameters.

Figure 5:
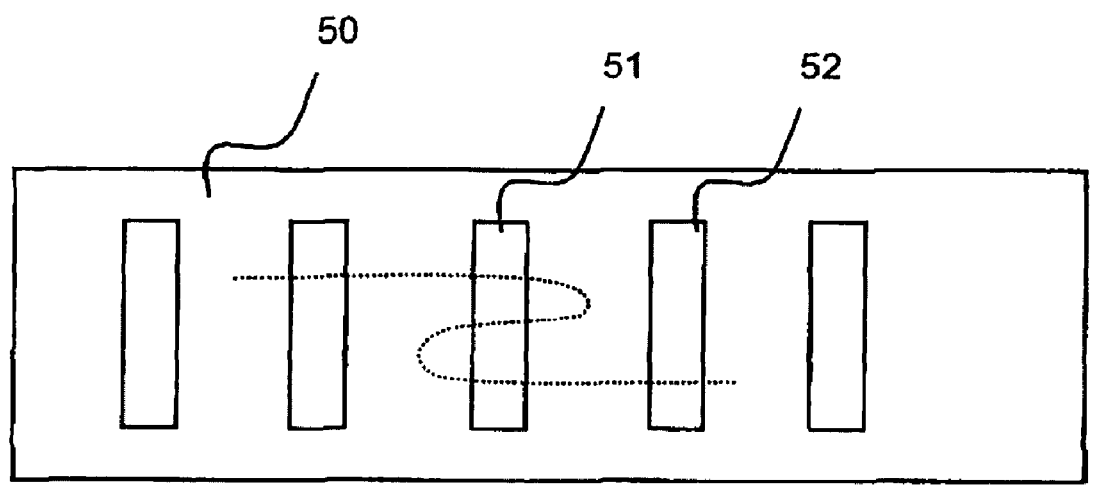
FIG. 5 shows a schematic diagram of a scanning process, in which an assay region on a dry-chemical test element is optically scanned again after a first scanning process.

FIG. 5 shows a schematic diagram of a scanning process, in which an assay region 51 on a dry-chemical test element 50 is optically scanned again after a first scanning process, before a subsequent assay region 52 is then scanned. In this way, it is possible to react during the optical scanning process if it is ascertained during the scanning of the assay region 51 that the light intensity initially received is not sufficient to generate a signal suitable for analysis on the detector device.

The above description concerned optical scanning using test light beams which are applied to the assay regions in which the optically active substances to be analyzed are present in immobilized form, in order thus to produce measurement light beams which may be in particular transmitted light beams, reflected light beams or emitted light beams. As an alternative or in addition, for the analysis of the dry-chemical test element 1, the generation of measurement light beams which are subsequently detected may be based on a bioluminescence, a chemoluminescence or an electro-chemoluminescence. The setting of a set of scanning parameters may then take place according to what has been described above.

The features of the invention which are disclosed in the above description, the claims and the drawing may be important both individually and in any combination for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method for analyzing a dry-chemical test element, in particular an immunological test element, in which a dry-chemical test element is analyzed by optical scanning, whereby measurement light beams leaving assay regions of the test element, which are loaded with one or more immobilized optically active substances, with a respective measurement light intensity are detected by a detector device, the method comprising the following steps:

during the optical scanning of a first assay region, from which the measurement light beams leave with a first measurement light intensity, a first quantity of light from measurement light beams which impinges on the detector device and a working range of the detector device are adapted to one another by selecting scanning parameters according to a first set of scanning parameters, and during the optical scanning of a second assay region, from which the measurement light beams leave with a second measurement light intensity which differs from the first measurement light intensity, a second quantity of light from measurement light beams which impinges on the detector device and the working range of the detector device are adapted to one another by selecting scanning parameters according to a second set of scanning parameters which differs from the first set of scanning parameters.

2. The method according to claim 1, characterized in that one or more variables selected from the following group of variables are set as scanning parameters: a scanning speed, an exposure time, a test light intensity of the test light beams, an amplification factor of the detector device and a supplying of the assay regions with electrical energy.

3. The method according to claim 1, characterized in that at least one scanning parameter is kept constant for the first and the second set of scanning parameters.

4. The method according to claim 1, characterized in that a change from the scanning parameters according to the first set of scanning parameters to the scanning parameters according to the second set of scanning parameters is carried out in the course of a continued scanning process for the dry-chemical test element.

5. The method according to claim 1, characterized in that the change from the scanning parameters according to the first set of scanning parameters to the scanning parameters according to the second set of scanning parameters takes place as a function of measurement information which is derived from a pre-scanning process carried out beforehand.

6. The method according to claim 1, characterized in that the change from the scanning parameters according to the first set of scanning parameters to the scanning parameters according to the second set of scanning parameters takes place as a function of current measurement information which is derived from current measured values during the optical scanning of the dry-chemical test element.

7. The method according to claim 1, characterized in that a changeover between the scanning parameters according to the first set of scanning parameters and the scanning parameters according to the second set of scanning parameters takes place multiple times during the optical scanning of the dry-chemical test element.

8. The method according to claim 1, characterized in that the first assay region, after the optical scanning with the scanning parameters according to the first set of scanning parameters, is optically scanned again with the scanning parameters according to the second set of scanning parameters.

9. The method according to claim 1, characterized in that test light application regions, which are respectively assigned to the assay regions, are formed in such a way as not to overlap during the optical scanning of the assay regions.

10. The method according to claim 1, characterized in that the first quantity of light is selected to lie in a first sub-range of the working range and the second quantity of light is selected to lie in a second sub-range of the working range which differs from the first sub-range.

11. The method according to claim 1, characterized in that a plurality of identical assay regions are optically scanned in one scanning position and are detected in a two-dimensionally resolved manner.

12. An apparatus for analyzing a dry-chemical test element, in particular an immunological test element, by optical scanning using a method according to at least one of the preceding claims, comprising:

a holder which is configured to hold a dry-chemical test element for analysis by optical scanning, a detector device which is configured to detect measurement light beams leaving assay regions, which are loaded with one or more immobilized optically active substances, with a respective measurement light intensity, and a control device which is configured to control the optical scanning of the dry-chemical test element as follows:

during the optical scanning of a first assay region, from which the measurement light beams leave with a first measurement light intensity, a first quantity of light from measurement light beams which impinges on the detector device and a working range of the detector device are adapted to one another by selecting scanning parameters according to a first set of scanning parameters, and during the optical scanning of a second assay region, from which the measurement light beams leave with a second measurement light intensity which differs from the first measurement light intensity, a second quantity of light from measurement light beams which impinges on the detector device and the working range of the detector device are adapted to one another by selecting scanning parameters according to a second set of scanning parameters which differs from the first set of scanning parameters.

13. The apparatus according to claim 12, characterized in that the control device is configured to set as scanning parameters one or more variables selected from the following group of variables: a scanning speed, an exposure time, a test light intensity of the test light beams, an amplification factor of the detector device and a supplying of the assay regions with electrical energy.

14. The apparatus according to claim 12, characterized in that the control device is configured to keep at least one scanning parameter constant for the first and the second set of scanning parameters.

15. The apparatus according to claim 12, characterized in that the control device is configured to carry out a change from the scanning parameters according to the first set of scanning parameters to the scanning parameters according to the second set of scanning parameters in the course of a continued scanning process for the dry-chemical test element.

16. The apparatus according to claim 12, characterized in that the control device is configured to initiate the change from the scanning parameters according to the first set of scanning parameters to the scanning parameters according to the second set of scanning parameters as a function of measurement information which is derived from a pre-scanning process carried out beforehand.

17. The apparatus according to claim 12, characterized in that the control device is configured to initiate the change from the scanning parameters according to the first set of scanning parameters to the scanning parameters according to the second set of scanning parameters as a function of current measurement information which is derived from current measured values during the optical scanning of the dry-chemical test element.

18. The apparatus according to claim 12, characterized in that the control device is configured to change multiple times between the scanning parameters according to the first set of scanning parameters and the scanning parameters according to the second set of scanning parameters during the optical scanning of the dry-chemical test element.

19. The apparatus according to claim 12, characterized in that the control device is configured to optically scan the first assay region again, after the optical scanning with the scanning parameters according to the first set of scanning parameters, with the scanning parameters according to the second set of scanning parameters.

20. The apparatus according to claim 12, characterized in that the control device is configured to form test light application regions, which are respectively assigned to the assay regions, in such a way that they do not overlap during the optical scanning of the assay regions.

21. The apparatus according to claim 12, characterized in that the control device is configured to select the first quantity of light to lie in a first sub-range of the working range and to select the second quantity of light to lie in a second sub-range of the working range which differs from the first sub-range.

22. The apparatus according to claim 12, characterized in that the control device and the detector device are configured to optically scan in one scanning position a plurality of identical assay regions and to detect them in a two-dimensionally resolved manner.

23. The apparatus according to claim 12, characterized by a light source which is configured to produce test light beams and to apply these to assay regions of the dry-chemical test element in the holder.

24. The apparatus according to claim 12, characterized by an electrode device which can be coupled to the assay regions and is configured to supply electrical energy to the assay regions of the dry-chemical test element.

* * * * *